United States Patent
Amino et al.

(10) Patent No.: US 6,630,191 B1
(45) Date of Patent: *Oct. 7, 2003

(54) ASPARTYL DIPEPTIDE ESTER DERIVATIVES AND SWEETENERS

(75) Inventors: Yusuke Amino, Kawasaki (JP);
Kazuko Yuzawa, Kawasaki (JP);
Tadashi Takemoto, Kawasaki (JP);
Ryoichiro Nakamura, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/736,149

(22) Filed: Dec. 15, 2000

Related U.S. Application Data

(63) Continuation of application No. PCT/JP99/03050, filed on Jun. 7, 1999.

(30) Foreign Application Priority Data

Jun. 26, 1998 (JP) ............................................ 10-180204

(51) Int. Cl.$^7$ ................................................ A23L 1/236
(52) U.S. Cl. ..................... 426/548; 558/411; 562/433
(58) Field of Search .......................... 426/548; 558/411, 558/418; 562/433, 442, 450; 560/125

(56) References Cited

U.S. PATENT DOCUMENTS

| | | | |
|---|---|---|---|
| 5,480,668 A | 1/1996 | Nofre et al. | |
| 5,773,640 A | 6/1998 | Nofre et al. | |
| 5,968,581 A | 10/1999 | Nakamura et al. | |

FOREIGN PATENT DOCUMENTS

| | | |
|---|---|---|
| EP | 0866073 | 9/1998 |
| JP | 10259194 | 9/1998 |

*Primary Examiner*—Leslie Wong
(74) *Attorney, Agent, or Firm*—Oblon, Spivak, McClelland, Maier & Neustadt, P.C.

(57) ABSTRACT

The present invention relates to novel, aspartyl dipeptide ester derivatives and salts thereof, such as N-[N-(3-(3-hydroxy-4-methoxyphenyl)propyl]-L-α-aspartyl]-L-(α-methyl)phenylalanine 1-methyl ester which provide high degrees of sweetness in comparison to conventional products, compositions and products containing the novel aspartyl dipeptide ester derivatives and method of producing the novel aspartyl dipeptide ester derivatives.

19 Claims, No Drawings

ASPARTYL DIPEPTIDE ESTER DERIVATIVES AND SWEETENERS

The present application is a Continuation application of PCT/JP99/03050 filed Jun. 7, 1999, the contents of which are herein incorporated by reference.

BACKGROUND OF THE INVENTION

1. Field of the Invention

The present invention relates to novel aspartyl dipeptide ester derivatives, and sweeteners and products such as foods which contain the same as an active ingredient.

2. Description of the Related Art

In recent years, as eating habits and products eaten have changed, fatness caused by excessive intake of sugar and diseases caused by fatness have been of significant concern. Accordingly, the development of a low-calorie sweetener that replaces sugar has been in demand. A sweetener that has been widely used is aspartame which is excellent in regarding both safety and taste properties. However, there are some problems of the aspartame with regard to its stability. WO 94/11391 states that derivatives in which an alkyl group is introduced on the amino group of aspartic acid constituting aspartame markedly improves sweetening potency and also results in a slight improvement in the stability of the compound. The best compound described in this document is N-[N-(3,3-dimethylbutyl)-L-α--aspartyl]-L-phenylalanine 1-methyl ester having a 3,3-dimethylbutyl group as an alkyl group which has a sweetening potency 10,000 times that of sugar.

Aspartame derivatives having 20 different substituents other than the 3,3-dimethylbutyl group are also disclosed where the derivatives have sweetening potencies less than 2,500 times that of sugar. Derivatives having a 3-(substituted phenyl)propyl group as an alkyl group are also shown. However, it is reported that the sweetening potency of N-[N-(3-phenylpropyl)-L-α-aspartyl]-L-phenylalanine 1-methyl ester is 1,500 times that of sugar and that of N-[N-[3-(3-methoxy-4-hydroxyphenyl)propyl]-L-α-aspartyl]-L-phenylalanine 1-methyl ester is 2,500 times that of sugar. These sweetening potencies are far less than that of N-[N-(3,3-dimethylbutyl)-L-α-aspartyl)-L-phenylalanine 1-methyl ester, 10,000 times. Furthermore, N-[N-(3,3-dimethylbutyl)-L-α-aspartylI-L-tyrosine 1-methyl ester is stated therein as an example of the derivatives in which L-phenylalanine methyl ester is replaced by the other amino acid ester, and it is reported that its sweetening potency is 4,000 times that of sugar.

Under these circumstances, development of a low-calorie sweetener having fine sweetening potency is in demand.

A problem to be solved by the present invention is to provide novel aspartyl dipeptide ester derivatives which are excellent in the safety and which have sweetening potency equal to or higher than that of the N-[N-(3,3-dimethylbutyl)-L-α-aspartyl]-L-phenylalanine 1-methyl ester, a low-calorie sweetener containing the same as an active ingredient and products, such as foods, containing the sweetener.

SUMMARY OF THE MENTION

In order to solve the problem, the present inventors have synthesized several aspartame derivatives in which various 3-(substituted phenyl) propyl group are introduced onto a nitrogen atom of aspartic acid constituting the aspartame derivatives, wherein a moiety of L-Phenylalanine methyl ester in the aspartame is replaced by another amino acid ester, through reductive alkylation by use of cinnamaldehydes having various substituent and which are readily available, or 3-phenylpropionaldehyde having various substituent that can easily derived therefrom as precursor aldehyde, and have examined the sweetening potency of them. The Inventors have discovered that with respect to the sweetening potency, the novel compounds have a far higher sweetening potency than N-[N-(3,3-dimethylbutyl)-L-α-aspartyl]-L-tyrosine 1-methyl ester which is reported to have the sweetening potency of 4,000 times that of sugar in WO 94/11391 and N-(N-(3,3-dimethylbutyl)-L-α-aspartyl]-L-phenylalanine 1-methyl ester which is reported therein to have the potency of 10,000 times that of sugar. Particularly, the compounds represented by the following formula (1) are excellent as sweeteners. These findings have led to the completion of the present invention.

The present invention is directed to novel aspartyl dipeptide ester derivatives (including the salts thereof) represented by the following formula (1):

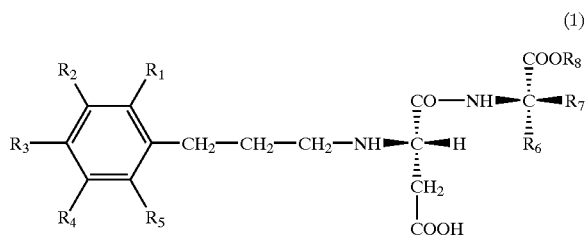

wherein;

$R_1$, $R_2$, $R_3$, $R_4$ and $R_5$, independently from each other, each represents a substituent selected from a hydrogen atom (H), a hydroxyl group (OH), an alkoxy group having from 1 to 3 carbon atoms ($OCH_3$, $OCH_2CH_3$, $OCH_2CH_2CH_3$, etc.), an alkyl group having from 1 to 3 carbon atoms ($CH_3$, $CH_2CH_3$, $CH_2CH_2CH_3$, etc.) and a hydroxyalkyloxy group having 2 or 3 carbon atoms ($O(CH_2)_2OH$, $OCH_2CH(OH)CH_3$, etc.), or $R_1$ and $R_2$, or $R_2$ and $R_3$ together form a methylenedioxy group ($OCH_2O$) wherein $R_4$, $R_5$, and $R_1$ or $R_3$ which does not form the methylenedioxy group, independently from each other, each represents any substituent as mentioned above designated for the $R_1$, $R_3$, $R_4$ and $R_5$, respectively; $R_6$ represents a substituent selected from a hydrogen atom, a benzyl group ($CH_2C_6H_5$), a p-hydroxybenzyl group ($CH_2C_6H_4$-p-OH), a cyclohexylmethyl group ($CH_2C_6H_{11}$), a phenyl group ($C_6H_5$), a cyclohexyl group ($C_6H_{11}$), a phenylethyl group ($CH_2CH_2C_6H_5$) and a cyclohexylethyl group ($CH_2CH_2C_6H_{11}$); $R_7$ represents a substituent selected from a hydrogen atom, a methyl group ($CH_3$), an ethyl group ($CH_2CH_3$), and an isopropyl group ($CH(CH_3)_2$); $R_8$ represents a substituent selected from a methyl group, an ethyl group, an isopropyl group, a n-propyl group ($CH_2CH_2CH_3$) and a t-butyl group ($C(CH_3)_3$); provided the derivatives in which $R_6$ represents a benzyl group and $R_7$ represents a hydrogen atom at the same time, and the derivatives in which $R_8$ represents a p-hydroxybenzyl group and $R_7$ represents a hydrogen atom at the same time are excluded.

DETAILED DESCRIPTION OF THE PREFERRED EMBODIMENTS

The novel aspartyl dipeptide ester derivatives of the present invention include the compounds represented by the above formula (1) and the salts thereof.

Preferred in the novel aspartyl dipeptide ester derivatives is the L-isomer of aspartic acid, whereas other amino acids may be L- or D-isomer forms.

In the compounds described above of the present invention, the following inventions are included as the embodiments for the preferable compounds:

(A) The compounds of formula (1) wherein $R_7$ is a substituent selected from a methyl group, an ethyl group and an isopropyl group; $R_1$, $R_2$, $R_3$, $R_4$ and $R_5$, independently from each other, each is a substituent selected from a hydrogen atom, a hydroxyl group, an alkoxy group having from 1 to 3 carbon atoms, an alkyl group having from 1 to 3 carbon atoms and a hydroxyalkyloxy group having 2 or 3 carbon atoms (for example, $O(CH)_2OH$, $OCH_2CH(OH)CH_3$, etc.), or $R_1$ and $R_2$, or $R_2$ and $R_3$ together form a methylenedioxy group ($OCH_2O$) wherein $R_4$, $R_5$ and, $R_1$ or $R_3$ which does not form the methylenedioxy group, independently from each other, each is a substituent selected from any substituent as mentioned above designated or exemplified for the $R_1$, $R_3$, $R_4$ and $R_5$; $R_6$ is a substituent selected from a hydrogen atom, a benzyl group, p-hydroxybenzyl group, a cyclohexylmethyl group, a phenyl group, a cyclohexyl group, a phenylethyl group and a cyclohexylethyl group; $R_8$ is a substituent selected from a methyl group, an ethyl group, an isopropyl group, a n-propyl group and a t-butyl group.

(B) The compounds of formula (1) wherein $R_6$ is a substituent selected from a hydrogen atom, a cyclohexylmethyl group, a phenyl group, a cyclohexyl group, a phenylethyl group and a cyclohexylethyl group; $R_1$, $R_2$, $R_3$, $R_4$ and $R_5$, independently from each other, each is a substituent selected from a hydrogen atom, a hydroxyl group, an alkoxy group having from 1 to 3 carbon atoms, an alkyl group having from 1 to 3 carbon atoms and a hydroxyalkyloxy group having 2 or 3 carbon atoms (for example, $O(CH_2)_2OH$, $OCH_2CH(OH)CH_3$, etc.), or $R_1$ and $R_2$, or $R_2$ and $R_3$ together form a methylenedioxy group ($OCH_2O$) wherein $R_4$, $R_5$ and, $R_1$ or $R_3$ which does not form the methylenedioxy group, independently from each other, each is a substituent selected from any substituent as mentioned above designated or exemplified for the $R_1$, $R_3$, $R_4$ and $R_5$, respectively; $R_7$ is a substituent selected from a hydrogen atom, a methyl group, an ethyl group and an isopropyl group; $R_8$ is a substituent selected from a methyl group, an ethyl group, an isopropyl group, a n-propyl group and a t-butyl group.

(C) The compounds of formula (1) wherein $R_2$ is a hydroxyl group, $R_3$ is a methoxy group, $R_1$, $R_4$ and $R_5$ are hydrogen atoms, $R_6$ is a benzyl group, and $R_7$ and $R_8$ are methyl groups.

(D) The compounds of formula (1) wherein $R_2$ is a methoxy group, $R_3$ is a hydroxyl group, $R_1$, $R_4$ and $R_5$ are hydrogen atoms, $R_6$ is a benzyl groups and $R_7$ and $R_8$ are methyl groups.

(C) The compounds of formula (1) wherein $R_2$ is a hydroxyl group, $R_3$ is a methoxy group, $R_1$, $R_4$, $R_5$ and $R_7$ are hydrogen atoms, $R_6$ is a cyclohexylmethyl group, and $R_8$ is a methyl group.

(D) The compounds of formula (1) wherein $R_2$ is a methoxy group, $R_3$ is a hydroxyl group, $R_1$, $R_4$, $R_5$ and $R_7$ are hydrogen atoms, $R_6$ is a cyclohexylmethyl group, and $R_8$ is a methyl group.

(E) The compounds of formula (1) wherein $R_2$ is a hydroxyl group, $R_3$ is a methoxy group, $R_1$, $R_4$, $R_5$ and $R_7$ are hydrogen atoms, $R_6$ is a phenyl group, and $R_8$ is a methyl group.

(F) The compounds of formula (1) wherein $R_2$ is a methoxy group, $R_3$ is a hydroxyl group, $R_1$, $R_4$, $R_5$ and $R_7$ are hydrogen atoms, $R_6$ is a phenyl group, and $R_8$ is a methyl group.

(G) The compounds of formula (1) wherein $R_2$ is a hydroxyl group, $R_3$ is a methoxy group, $R_1$, $R_4$, $R_5$ and $R_7$ are hydrogen atoms, $R_6$ is a 2-phenylethyl group, and $R_8$ is a methyl group.

(H) The compounds of formula (1) wherein $R_2$ is a methoxy group, $R_3$ is a hydroxyl group, $R_1$, $R_4$, $R_5$ and $R_7$ are hydrogen atoms, $R_6$ is a 2-phenylethyl group, and $R_8$ is a methyl group.

(I) The compounds of formula (1) wherein $R_2$ is a hydroxyl group, $R_3$ is a methoxy group, $R_1$, $R_4$, $R_5$ and $R_6$ are hydrogen atoms, $R_7$ is a methyl group, and $R_8$ is a n-propyl group.

(J) The compounds of formula (1) wherein $R_2$ is a methoxy group, $R_3$ is a hydroxyl group, $R_1$, $R_4$, $R_5$ and $R_6$ are hydrogen atoms, $R_7$ is a methyl group, and $R_8$ is a n-propyl group.

(K) The compounds of formula (1) wherein $R_1$ is a hydroxyl group, $R_3$ is a methoxy group, $R_2$, $R_4$, and R are hydrogen atoms, $R_6$ is a benzyl group, and $R_7$ and $R_8$ are methyl groups.

(L) The compounds of formula (1) wherein $R_2$ and $R_8$ are methyl groups, $R_3$ is a hydroxyl group, $R_1$, $R_4$, $R_5$ and $R_7$ are hydrogen atoms, and $R_6$ is a cyclohexylmethyl group.

(M) The compounds of formula (1) wherein $R_1$ is a hydroxyl group, $R_3$ and $R_8$ are methyl groups, $R_2$, $R_4$, $R_5$ and $R_7$ are hydrogen atoms, and $R_6$ is a cyclohexylmethyl group.

The present invention also provides sweeteners containing at least one of the above disclosed compounds as an active ingredient. The sweeteners may also contain a carrier or bulking agent.

The present invention also provides foods or other products requiring added sweetness.

The present invention also provides methods for imparting sweetness by incorporating or giving (adding, mixing, or the like) at least one of the compounds of formula (1) to products requiring the sweetness such as foods, drinks (beverages), pharmaceutical products, oral hygiene products and the like.

In a method for producing compounds of the general formula (1) described above, an aldehyde represented by the following general formula (2) or (3) is reacted with an aspartame derivative represented by the following formula (4) under reductive alkylation conditions.

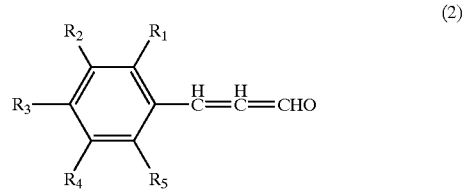

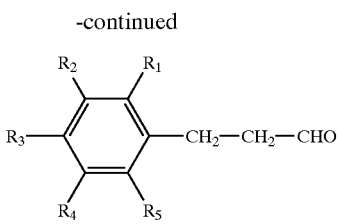

(3)

wherein $R_1$, $R_2$, $R_3$, $R_4$ and $R_5$ have the same meanings as those in the $R_1$, $R_2$, $R_3$, $R_4$ and $R_5$ mentioned in the above formula (1) for the derivatives in the present invention.

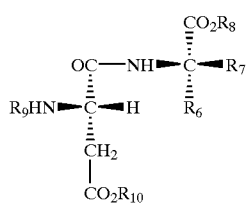

(4)

wherein $R_6$, $R_7$ and $R_8$ have the same meanings as those in the $R_6$, $R_7$ and $R_8$ mentioned in the above general formula (1) for the derivatives in the present invention; $R_9$ represents a substituent selected from a hydrogen atom and a substituent which is convertible to a hydrogen atom under reductive alkylation conditions; and $R_{10}$ represents a substituent selected from a hydrogen atom and a substituent which can be used for protecting a carboxyl group, such as a benzyl group and a t-butyl group.

Said method comprises the step of reacting under any reductive alkylation conditions, and may further comprise additional steps, for example, to obtain the compound of general formula (1) such steps for removing protective groups and forming salts after the step of reacting under the reductive alkylation conditions, if necessary.

As said substituent which is convertible to a hydrogen atom under the reductive alkylation conditions, any substituent which meets said condition can be selected from known substituents therefor, for example, a benzyloxycarbonyl group, a p-nitrobenzyloxycarbonyl group, a p-methoxybenzyloxycarbonyl group, a benzyl group, and dibenzyl groups (N,N-dibenzyl groups). The reductive alkylation conditions which are appropriate include those which are known in the art or those developed at a later time, for example, using a metal hydride.

In the above-disclosed method of producing compounds of formula (10 wherein one or more hydroxyl groups in the aldehyde represented by the above general formula (2) or (3) are protected by any appropriate protecting groups (for example, a benzyl group) in the case of the aldehyde having one or more hydroxyl groups.

Examples of salts of the present compounds include; alkaline metal salts such as sodium and potassium; alkaline earth metal salts such as calcium and magnesium; ammonium salts with ammonia; amino acid salts such as lysine and arginine; inorganic acid salts such as hydrochloric acid and sulfuric acid; and organic acid salts such as citric acid and acetic acid; and salts of other sweeteners such as saccharin, acesulfame, cyclamic acid, glycyrrhizic acid. These salts are included in the present derivatives.

The aspartyl dipeptide ester derivatives of the present invention can easily be formed by reductively alkylating aspartame derivatives, wherein a moiety of L-phenylalanine methyl ester in the aspartame is replaced by another amino acid ester, with cinnamaldehydes having various substituents and a reducing agent (for example, hydrogen/palladium carbon catalyst). Alternatively, the derivatives can be formed by subjecting aspartame derivatives (for example, β-O-benzyl(α-L-aspartyl-L-amino acid methyl ester) having a protective group in a carboxylic acid in the β-position which derivatives can be obtained by the usual peptide synthesis method (Izumiya et al., Basis of Peptide Synthesis and Experiments Thereof, Maruzen, published Jan. 20, 1985, the contents of which are incorporated by reference) to reductive alkylation with cinnamaldehydes having various substituents and a reducing agent (for example, $NaB(OAc)_3H$) (A. F. Abdel-Magid et al., Tetrahedron Letters, 31, 5595 (1990), the contents of which are incorporated by reference), and then removing the protective group. However, the method of forming the compounds of the present invention is not limited thereto. 3-Phenylpropionaldehydes having various substituents or acetal derivatives thereof can be used as precursor aldehydes in the reductive alkylation instead of cinnamaldehydes having various substituents.

As a result of sensory evaluations, the present compounds and the salts thereof were found to have a strong sweetening potency and have sensory (organoleptic) properties similar to that of sugar. For example, the sweetening potency of N-[N-[3-(3-hydroxy-4-methoxyphenyl)propyl]-L-α-aspartyl]-L-(α-methyl)phenylalanine 1-methyl ester was approximately 18,000 times (relative to sugar), that of N-[N-[3-(3-methoxy-4-hydroxyphenyl)propyl]-L-α-aspartyl]-L-(α-methy)phenylalanine 1-methyl ester was approximately 18,000 times (relative to sugar), that of N-[N-[3-(3-hydroxy-4-methoxyphenyl)propyl]-L-α-aspartyl]-3-cyclohexyl-L-alanine 1-methyl ester was approximately 25,000 times (relative to sugar), that of N-[N-[3-(3-methoxy-4-hydroxyphenyl)propyl]-L-α-aspartyl]-3-cyclohexyl-L-alanine 1-methyl ester was approximately 25,000 times (relative to sugar), that of N-[N-[3-(3-methyl-4-hydroxyphenyl)propyl]-L-(α-aspartyl]-3-cyclohexyl-L-alanine 1-methyl ester was approximately 40,000 times (relative to sugar).

With respect to the aspartyl dipeptide derivatives (represented by the following general formula (5)) formed, the structures and the results of the sensory evaluation are shown in Table 1.

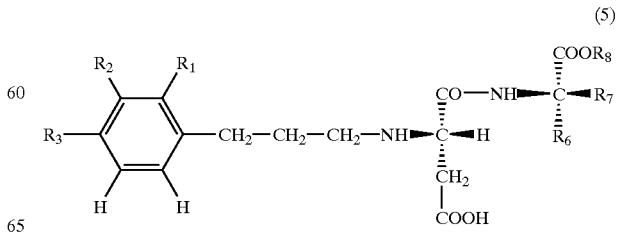

(5)

TABLE 1

Structures and sweetening potency of aspartyl dipeptide ester derivatives

| Compound Number | $R_1$ | $R_2$ | $R_3$ | $R_6$ | $R_7$ | $R_8$ | Sweetening Potency[1] |
|---|---|---|---|---|---|---|---|
| 1 | H | OH | $OCH_3$ | $CH_2C_6H_5$ | $CH_3$ | $CH_3$ | 18000 |
| 2 | H | $OCH_3$ | OH | $CH_2C_6H_5$ | $CH_3$ | $CH_3$ | 18000 |
| 3 | H | OH | $OCH_3$ | $CH_2C_6H_{11}$ | H | $CH_3$ | 25000 |
| 4 | H | $OCH_3$ | OH | $CH_2C_6H_{11}$ | H | $CH_3$ | 25000 |
| 5 | H | OH | $OCH_3$ | $C_6H_5$ | H | $CH_3$ | 1600 |
| 6 | H | $OCH_3$ | OH | $C_6H_5$ | H | $CH_3$ | 700 |
| 7 | H | OH | $OCH_3$ | $CH_2CH_2C_5H_5$ | H | $CH_3$ | 2000[2] |
| 8 | H | OCH3 | OH | $CH_2CH_2C_6H_5$ | H | $CH_3$ | 2400[2] |
| 9 | H | OH | $OCH_3$ | H | $CH_3$ | $CH_2CH_2CH_3$ | 800 |
| 10 | H | $OCH_3$ | OH | H | $CH_3$ | $CH_2CH_2CH_3$ | 600 |
| 11 | OH | H | $OCH_3$ | $CH_2C_6H_5$ | $CH_3$ | $CH_3$ | 15000 |
| 12 | H | $CH_3$ | OH | $CH_2C_6H_{11}$ | H | $CH_3$ | 40000 |
| 13 | OH | H | $CH_3$ | $CH_2C_6H_{11}$ | H | $CH_3$ | 25000 |

[1] Relative to sweetening potency of a 4% sucrose aqueous solution
[2] Compensated value as optical isomer As understood from the results of Table 1, the novel derivatives in the present invention have excellent sweetening potency.

When the derivatives (including compounds in the present invention and the salts thereof) of the present invention are used as sweeteners, these may of course be used in combination with other sweeteners as desired or needed.

When the derivatives of the present invention are used as sweeteners, an appropriate carrier and/or an appropriate bulking agent may be used as required. For example, a carrier, a bulking agent or the like which is known in the art and so far used for the sweeteners is available. The appropriate carriers or bulking agent may be selected from polydextrose, starch, maltodextrines, cellulose, methylcellulose, carboxymethylcellulose and other cellulose derivatives, sodium alginate, pectins, gums, lactose, maltose, glucose, sucrose, leucine, glycerole, mannitol, sorbitol, xylitol, erythritol, and equivalents thereof.

The derivatives of the present invention can be used as sweeteners or ingredients therefor, and further as sweeteners for products such as foods and the like to which a sweetness has to be imparted, for example, confectionery, chewing gum, hygiene products, toiletries, cosmetics, pharmaceutical products and veterinary products for animals. Still further, they can be used as a form of products having sweetness including the derivatives of the present invention and they can be used in a method of imparting sweetness to the products requiring sweetness. The method therefor can be, known methods for example, conventional methods for using a sweetening ingredient for a sweetener in the sweeteners or the method of imparting sweetness.

Having generally described this invention, a further understanding can be obtained by reference to certain specific examples which are provided herein for purposes of illustration only, and are not intended to be limiting unless otherwise specified.

This application is based on International Application Serial No PCT/JP99/03050, filed Jun. 7, 1999 and Japanese Patent Application Serial No. 10-180204, filed on Jun. 26, 1998, each of which are incorporated herein by references in their entirety.

In the following examples, NMR spectra were measured by using "Varian Gemini-300 (300 MHz)" and MS spectra were measured by using "Thermo Quest TSQ700".

EXAMPLES

Example 1

Synthesis of N-[N-[3-(3-Hydroxy-4-methoxyphenyl)propyl]-L-α-aspartyl]-L-(α-methyl) phenylalanine 1-Methyl Ester Twenty milliliters of methanol was cooled to 0° C. To this was added 1.09 ml (15.0 mmol) of thionyl chloride by dropping. Then 1.0 g (5.58 mmol) of L-(α-methyl) phenylalanine was added to the mixture and stirred for 1 hour at 0° C. and further over night at 70° C. The solvent was removed under reduced pressure. An aqueous solution of 5% sodium hydrogen carbonate was added to the residue and extracted twice with 50 ml of methylene chloride. The organic layer was dried over anhydrous magnesium sulfate and magnesium sulfate was removed by filtration. The filtrate was concentrated under reduced pressure to obtain 0.95 g (4.92 mmol) of L-(α-methyl)phenylalanine methyl ester as an oil.

To 30 ml of methylene chloride were added 0.95 g (4.92 mmol) of L-(α-methyl)phenylalanine methyl ester and 1.59 g (4.92 mmol) of N-t-butoxycarbonyl-L-aspartic acid β-benzyl ester. The mixture was cooled to 0° C. To the mixture, 730 mg (5.41 mmol) of 1-hydroxybenzotriazol hydrate (HOBT) and 1.04 g (5.41 mmol) of water-soluble carbodiimide hydrochloride were added and stirred at 0° C. for 1 hour and further at room temperature over night. The reaction mixture was concentrated under reduced pressure and 50 ml of water was added to the residue and the mixture was extracted twice with 50 ml of ethyl acetate. The organic layer was washed twice with 50 ml of 5% aqueous solution of citric acid, once with 50 ml of saturated aqueous solution of sodium chloride, twice with 50 ml of 5% sodium hydrogen carbonate aqueous solution, then once 50 ml of saturated aqueous solution of sodium chloride. Then the organic layer was dried over anhydrous magnesium sulfate and magnesium sulfate was removed by filtration. And the filtrate was concentrated to obtain 2.07 g (4.15 mmol) of N-t-butoxycarbonyl-β-O-benzyl-α--L-aspartyl-L-(α-methyl) phenylalanine methyl ester as a viscous oil.

Ten milliliters of a solution of 4N-HCl/dioxane were added to 1.04 g (2.08 mmol) of N-t-butoxycarbonyl-β-O-benzyl-α-L-aspartyl-L-(α-methyl)phenylalanine methyl ester, and the mixture was stirred at room temperature for 1 hour. The reaction solution was concentrated under reduced pressure. Fifty milliliters of 5% sodium hydrogen carbonate aqueous solution was added to the residue, and the mixture was extracted twice with 50 ml of ethyl acetate. The organic layer was washed with a saturated aqueous solution of sodium chloride, and dried over anhydrous magnesium sulfate. Then, magnesium sulfate was removed by filtration, and the filtrate was concentrated under reduced pressure to obtain 822 mg (2.06 mmol) of β-O-benzyl-α-L-aspartyl-L-(α-methyl)phenylalanine methyl ester as a viscous oil.

The β-O-benzyl-α-L-aspartyl-L-(α-methyl) phenylalanine methyl ester (822 mg, 2.06 mmol) was dissolved in 20 ml of tetrahydrofuran (THF), and the solution was maintained at 0° C. To this were added 554 mg (2.06 mmol) of 3-benzyloxy-4-methoxycinnamaldehyde, 0.11 ml (2.06 mmol) of acetic acid and 636 mg (3.0 mmol) of NaB (OAc)$_3$H. The mixture was stirred at 0° C. for 1 hour and further overnight at room temperature. To the reaction solution was added 50 ml of a saturated aqueous solution of sodium hydrogen carbonate, and the mixture was extracted twice with 50 ml of ethyl acetate. The organic layer was washed with a saturated aqueous solution of sodium chloride, and dried over anhydrous magnesium sulfate. Then, magnesium sulfate was removed by filtration, and the filtrate was concentrated under reduced pressure. The residue was purified with PTLC Preparative Thin Layer Chromatography) to obtain 1.17 g (1.80 mmol) of N-[N-[3-(3-benzyloxy-4-methoxyphenyl)propenyl]-β-benzyl-L-α-aspartyl]-L-(α-methyl)phenylalanine 1-methyl ester as a viscous oil.

The N-[N-(3-(3-benzyloxy-4-methoxyphenyl)propenyl]-β-O-benzyl-L-α-aspartyl]-L-(α-methyl)phenylalanine 1-methyl ester (1.173 g, 1.78 mmol) was dissolved in a mixed solvent of 30 ml of methanol and 1 ml of water, and 350 mg of 10% palladium carbon (water content 50%) were added thereto. The mixture was reduced in a hydrogen stream at room temperature for 3 hours. The catalyst was removed by filtration, and the filtrate was concentrated under reduced pressure. In order to remove an odor adsorbed, the residue was purified with PTLC to obtain 553 mg (1.17 mmol) of N-[N-(3-(3-hydroxy4-methoxyphenyl) propyl]-L-α-aspartyl]-L-(α-methyl)phenylalanine 1-methyl ester as a solid.

$^1$HNMR (DMSO-d$_6$) δ:1.27 (s,3H), 1.60–1.72 (m,2H), 2.30–2.60 (m, 6H), 3.10 (dd, 2H), 3.50–3.62 (m, 1H), 3.56 (s, 3H), 3.71 (s, 3H), 6.54 (dd, 1H), 6.61 (d, 1H, 6.79 (d, 1H), 7.04–7.10 (m,2H), 7.22–7.34 (m,3H), 8.40 (s,1H), 8.80 (brs,1H). ESI (Electrospray Ionization)-MS 473.3 (MH$^+$); Sweetening potency (relative to sugar): 18,000 times.

Example 2

Synthesis of N-(N-(3-(3-Methoxy-4-hydroxyphenyl) propyl]-L-α-aspartyl]-L-(α-methyl)phenylalanine 1-Methyl Ester Example 1 was repeated except that 3-methoxy-4-hydroxycinnamaldehyde was used instead of 3-benzyloxy-4-methoxycinnamaldehyde to obtain N-[N-[3-(3-methoxy-4-hydroxyphenyl)propyl]-L-α-aspartyl]-L-(α-methyl) phenylalanine 1-methyl ester in a total yield of 42.7% as a solid in the same manner as above.

$^1$HNMR (DMSO-d$_6$) δ:1.28 (s,3H), 1.60–1.72 (m,2H), 2.24–2.58 (m,6H), 3.14 (dd,2H), 3.43–3.50 (m,1H), 3.56 (s,3H), 3.74 (s, 3H), 6.56 (d, 1H), 6.65 (d, 1H), 7.07 (d, 2H), 7.20–7.32 (m, 3H) 8.33 (s,1H), 8.65 (brs,1H). ESI-MS 473.3 (MH$^+$) Sweetening potency (relative to sugar): 18,000 times.

Example 3

Synthesis of N-[N-[3-(3-Hydroxy-4-methoxyphenyl)propyl]-L-α-aspartyl]-3-cyclohexyl-L-alanine 1-Methyl Ester Example 1 was repeated except that 3-cyclohexyl-L-alanine was used instead of L-(α-methyl)-phenylalanine to obtain N-[N-[3-(3-hydroxy-4-methoxyphenyl)propyl]-L-α-aspartyl]-3-cyclohexyl-L-alanine 1-methyl ester in a total yield of 30.0% as a solid in the same manner as above.

$^1$HNMR (DMSO-d$_6$) (δ:1.11 (m,2H), 1.64 (m,10H), 2.27 (m,1H), 2.38 (m, 1H), 2.45 (m, 4H), 3.38 (m, 2H), 3.51 (m, 1H), 3.61 (s, 3H), 3.71 (s, 3H), 4.37 (m, 1H), 6.57 (m,2H), 6.78 (m, 1H), 8.47 (m, 1H), ESI-MS 465.3 (MH$^+$) Sweetening potency (relative to sugar): 25,000 times.

Example 4

Synthesis of N-[N-(3-(3-Methoxy-4-hydroxyphenyl) propyl]-L-α-aspartyl]-3-cyclohexyl-L-alanine 1-Methyl Ester Example 1 was repeated except that 3-cyclohexyl-L-alanine was used instead of L-(α-methyl)-phenylalanine and that 3-methoxy-4-benzyloxycinnamaldehyde was used instead of 3-benzyloxy-4-methoxycinnamaldehyde to obtain N-(N-[3-(3-methoxy-4-hydroxyphenyl)propyl)-L-α-aspartyl]-3-cyclohexyl-L-alanine 1-methyl ester in a total yield of 28.7% as a solid in the same manner as above.

$^1$HNMR (DMSO-d$_6$) (δ:1.10 (m, 2H), 1.62 (m, 10H), 2.25 (m, 1H), 2.38 (m, 1H), 2.49 (m, 4H), 3.38 (m, 2H), 3.52 (m, 1H), 3.60 (s, 3H), 3.73 (s,3H), 4.36 (m,1H, 6.63 (m,3H, 8.46 (M,1H). ESI-MS 465.3 (MH$^+$) Sweetening potency (relative to sugar): 25,000 times.

Example 5

Synthesis of N-[N-[3-(3-Hydroxy-4-methoxyphenyl)propyl]-L-α-aspartyl]-L-phenylglycin 1-Methyl Ester Example 1 was repeated except that L-phenylglycin was used instead of L-(α-methyl)-phenylalanine to obtain N(N-[3-(3-hydroxy-4-methoxyphenyl)propyl]-L-α-aspartyl]-L-phenylglycin 1-methyl ester in a total yield of 19. 0% as a solid in the same manner as above.

$^1$HNMR (DMSO-d$_6$) δ:1.63 (m, 2H), 2.30 (m, 1H), 2.42 (m, 1H), 2.48 (m, 4H), 3.38 (m, 1H), 3.63 (s, 3H), 3.71 (s, 3H), 5.44 (m, 1H), 6.55 (m,2H), 6.78 (m,1H), 7.38 (m,5H), 8.96 (M,1H). ESI-MS 445.3 (MH$^+$) Sweetening potency (relative to sugar): 1,600 times.

Example 6

Synthesis of N-[N-[3-(3-Methoxy-4-hydroxyphenyl) propyl]-L-α-aspartyl]-L-phenylglycin 1-Methyl Ester Example 1 was repeated except that L-phenylglycin was used instead of L-α-methyl)-phenylalanine and that 3 methoxy-4-benzyloxycinnamaldehyde was used instead of 3-benzyloxy-4-methoxycinnamaldehyde to obtain N-[N-[3-(3-methoxy-4-hydroxyphenyl)propyl]-L-α-aspartyl]-L-phenylglycin 1-methyl ester in a total yield of 23.5% as a solid in the same manner as above.

$^1$HNMR (DMSO-d$_6$) (δ:1.65 (m, 2H), 2.29 (m, 1H), 2.43 (m, 1H), 2.50 (m, 4H), 3.58 (m, 1H), 3.63 (s, 3H), 3.73 (s, 3H), 5.44 (M, 1H), 6.41 (m,3H), 7.38 (m,5H), 8.94 (m,1H). ESI-MS 445.3 (MH$^+$) Sweetening potency (relative to sugar): 700 times.

Example7

Synthesis of N-[N-[3-(3-Hydroxy-4-methoxyphenyl)propyl]-L-α-aspartyl]-DL-homophenylalanine 1-Methyl Ester Example 1 was repeated except that DL-homophenylalanine was used instead of L-(α-methyl)- phenylalanine to obtain N-[N-[3-(3-hydroxy-4-methoxyphenyl)propyl]-L-α-aspartyl]-DL-homophenylalanine 1-methyl ester in a total yield of 16.7% as a solid in the same manner as above.

$^1$HNMR (DMSO-d$_6$) (δ:1.68 (m, 2H), 1.96 (m, 2H) 2.32 (m, 1H), 2.46 (m, 1H), 2.58 (m, 4H), 3.37 (m, 2H), 3.52 (m, 1H), 3.60 (2s, 3H), 3.70 (2s, 3H), 4.21 (m, 1H), 6.68 (m, 3H), 7.23 (m, 5H), 8.58 (m,1H). ESI-MS 473.3 (MH$^+$) Sweetening potency (relative to sugar): 1,000 times.

Example 8

Synthesis of N-[N-[3-(3-Methoxy-4-hydroxyphenyl)propyl]-L-α-aspartyl]-DL-homophenylalanine 1-Methyl Ester Example 1 was repeated except that DL-homophenylalanine was used instead of L-(α-methyl)-phenylalanine and that 3-methoxy-4-benzyloxycinnamaldehyde was used instead of 3-benzyloxy-4-methoxycinnamaldehyde to obtain N-(N-[3-(3-methoxy-4-hydroxyphenyl)propyl]-L-α-aspartyl]-DL-homophenylalanine 1-methyl ester in a total yield of 18.4% as a solid in the same manner as above.

$^1$HNMR (DMSO-d$_6$) (δ:1.70 (m, 2H), 1.96 (m, 2H), 2.34 (m, 1H), 2.45 (m, 1H), 2.56 (m, 4H), 3.40 (m, 2H), 3.55 (m, 1H), 3.60 (2s, 3H), 3.70 (2s, 3H), 4.21 (m, 1H), 6.68 (m, 3H), 7.23 (m, 5H) 8.58 (M,1H). ESI-MS 473.3 (MH$^+$) Sweetening potency (relative to sugar): 1,200 times.

Example 9

Synthesis of N-[N-[3-(3-Hydroxy-4-methoxyphenyl)propyl]-L-α-aspartyl]-D-alanine 1-n-Propyl Ester Example 1 was repeated except that D-alanine n-propyl ester hydrochloride was used instead of L-(α-methyl) phenylalanine methyl ester to obtain N-[N-[3-(3-hydroxy-4-methoxyphenyl)propyl]-L-α-aspartyl]-D-alanine 1-n-propyl ester in a total yield of 37.3% as a solid in the same manner as above.

$^1$HNMR (DMSO-d$_6$) (δ:0.87 (t,3H), 1.28 (d,3H), 1.50–1.60 (m,2H), 1.60–1.70 (m,2H), 2.18–2.60 (m,6H), 3.43–3.51 (m,1H), 3.71 (s,3H), 3.95–4.02 (m,2H), 4.20–4.30 (m,1H, 6.54 (d,1H), 6.61 (s,1H), 6.78 (d,1H), 8.50 (d,1H), 8.80 (brs,1H). ESI-MS 411.4 (MH$^+$) Sweetening potency (relative to sugar): 800 times.

Example 10

Synthesis of N-[-[3-(3-Methoxy-4-hydroxyphenyl)propyl]-α-aspartyl]-D-alanine 1-n-Propyl Ester Example 1 was repeated except that D-alanine n-propyl ester hydrochloride was used instead of L-(α-methyl) phenylalanine methyl ester and that 3-methoxy-4-hydroxycinnamaldehyde was used instead of 3-benzyloxy-4-methoxycinnamaldehyde to obtain N-[N-[3-(3-methoxy-4-hydroxyphenyl)propyl]-L-α-aspartyl]-D-alanine 1-n-propyl ester in a total yield of 27.8% as a solid in the same manner as above.

$^1$HNMR (DMSO-d$_6$) δ:0.87 (t,3H), 1.28 (d,3H), 1.50–1.62 (m,2H), 1.62–1.73 (m,2H), 2.20–2.60 (m,6H), 3.45–3.51 (M,1H), 3.74 (s,3H), 3.94–4.02 (m,2H), 4.20–4.30 (m,1H), 6.56(dd,1H), 6.65 (d,1H), 6.74 (d,1H), 8.51 (d,1H), 8.60 (brs,1H). ESI-MS 411.4 (MH$^+$) Sweetening potency (relative to sugar): 600 times.

Example 11

Synthesis of N-[N-[3-(2-Hydroxy-4-methoxyphenyl)propyl]-L-α-aspartyl]-L-(α-methyl) Phenylalanine 1-Methyl Ester Example 1 was repeated except that 2-benzyloxy-4-methoxycinnamaldehyde was used instead of 3-benzyloxy-4-methoxycinnamaldehyde to obtain N-[N-[3-(2-hydroxy-4-methoxyphenyl)propyl]-L-α-aspartyl]-L-(α-methyl) phenylalanine 1-methyl ester in a total yield of 44.0% as a solid in the same manner as above.

$^1$HNMR (DMSO-d$_6$) δ1.27 (s, 3H), 1.58–1.68 (m, 2H), 2.23–2.33 (dd, 1H), 2.35–2.48 (m, 5H), 3.03 (d, 1H), 3.25 (d, 1H), 3.43–3.48 (m, 1H), 3.56 (s, 3H), 3.65 (s, 3H), 6.28 (dd, 1H), 6.35 (d, 1H), 6.92 (d, 1H), 7.05–7.10 (m, 2H), 7.20–7.31 (m, 3H), 8.35 (s, 1H). ESI-MS 473.2 (MH$^+$) Sweetening potency (relative to sugar): 15,000 times.

Example 12

Synthesis of N-[N-(3-(3-Methyl-4-hydroxyphenyl)propyl]-L-α-aspartyl]-3-cyclohexyl-L-anine 1-Methyl Ester Example 1 was repeated except that 3-cyclohexyl-L-alanine was used instead of L-(α-methyl)-phenylalanine and that 3-methyl-4-benzyloxycinnamaldehyde was used instead of 3-benzyloxy-4-methoxycinnamaldehyde to obtain N-(N-[3-(3-methyl-4-hydroxyphenyl)propyl-L-α-aspartyl]-3-cyclohexyl-L-alanine 1-methyl ester in a total yield of 35.6% as a solid in the same manner as above.

$^1$HNMR (DMSO-d$_6$) (δ:0.83–1.65 (m,11 H), 1.49–1.60 (m,2H), 1.63–1.68 (m,2H), 2.08 (s,3H), 2.24–2.40 (m,2H), 2.41–2.51 (m,4H), 3.49–3.53 (m,1H), 3.61 (s,3H), 4.33–4.50 (m,1H, 6.65 (d, 1H), 6.78 (d, 1H), 6.86 (s, 1H), 8.48 (d, 1H), 9.04 (brs, 1H). ESI-MS 449.3 (MH$^+$) Sweetening potency (relative to sugar): 40,000 times.

Example 13

Synthesis of N-[N-(3-(2-Hydroxy-4-methylphenyl)propyl-L-α-aspartyl]-3-cyclohexyl-L-alanine Example 1 was repeated except that 3-cyclohexyl-L-alanine was used instead of L-(α-methyl)-phenylalanine and that 2-benzyloxy4-methylcinnamaldehyde was used instead of 3-benzyloxy-4-methoxycinnamaldehyde to obtain N-[N-[3-(2-hydroxy-4-methylphenyl)propyl]-L-α-aspartyl]-3-cyclohexyl-L-alanine in a total yield of 26.2% as a solid in the same manner as above.

$^1$HNMR (DMSO-d$_6$) δ:0.82–1.65 (m, 11H), 1.49–1.59 (m,2H), 1.61–1.66 (m,2H), 2.17 (s,3H), 2.23–2.41 (m,2H), 2.44–2.48 (m,4H), 3.47–3.53 (m,1H), 3.61 (s,3H), 4.33–4.41 (M, 1H), 6.50 (d, 1H), 6.59 (s, 1H), 6.89 (d, 1H), 8.50 (d, 1H), 9.12 (brs, 1H). ESI-MS 449.3 (MH$^+$) Sweetening potency (relative to sugar): 25,000 times.

Example 14

Synthesis of N-[N-[3-(3-Hydroxy-4-methoxyphenyl)propyl]-L-α-aspartyl]-L-(α-methyl)phenylalanine 1-Methyl Ester The reaction and the treatment are carried out in the same manner as in Example 1 except that 3-(3-benzyloxy-4-methoxyphenyl)propionaldehyde is used instead of 3-benzyloxy-4-methoxycinnamaldehyde to obtain N-(N-(3-(3-hydroxy-4-methoxyphenyl)propyl]-L-α-aspartyl]-L-(α-methyl)phenylalanine 1-methyl ester.

Effect of the Invention

The novel aspartyl dipeptide ester derivatives of the present invention are low in calories. And the derivatives have especially an excellent sweetening potency in comparison with conventional sweeteners. The present invention can provide novel chemical substances having excellent properties as sweeteners. Accordingly, such novel derivatives in the present invention can be used as sweeteners, and also can impart a sweetness to products such as drinks (beverages) and foods requiring a sweetness.

Obviously, numerous modifications and variations on the present invention are possible in light of the above teachings. It is therefore to be understood that within the scope of the appended claims, the invention may be practiced otherwise than as specifically described herein.

We claim:

1. A aspartyl dipeptide ester derivative and salts thereof represented by formula (1)

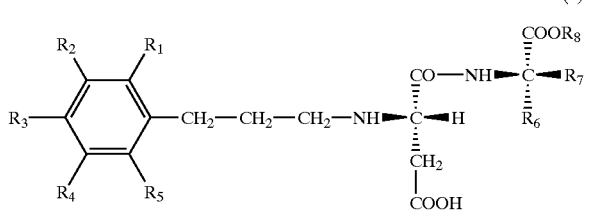

wherein;

$R_1$, $R_2$, $R_3$, $R_4$ and $R_5$, independently from each other, each represents a substituent selected from the group consisting of a hydrogen atom, a hydroxyl group, an alkoxy group having from 1 to 3 carbon atoms, an alkyl group having from 1 to 3 carbon atoms and a hydroxyalkyloxy group having 2 or 3 carbon atoms;

wherein, optionally, $R_1$ and $R_2$, or $R_2$ and $R_3$ together form a methylenedioxy group ($OCH_2O$) wherein $R_4$, $R_5$, and $R_1$ or $R_3$ which does not form the methylenedioxy group, independently from each other, are defined as above;

$R_6$ is selected from the group consisting of a hydrogen atom, a benzyl group ($CH_2C_6H_5$), a p-hydroxybenzyl group ($CH_2C_6H_4$-p-OH), a cyclohexylmethyl group ($CH_2C_6H_{11}$), a phenyl group ($C_6H_5$), a cyclohexyl group ($C_6H_{11}$), a phenylethyl group ($CH_2CH_2C_6H_5$) and a cyclohexylethyl group ($CH_2CH_2C_6H_{11}$);

$R_7$ is selected from a hydrogen atom, a methyl group ($CH_3$), an ethyl group ($CH_2CH_3$) and an isopropyl group ($CH(CH_3)_2$); $R_8$ represents a substituent selected from a methyl group, an ethyl group, an isopropyl group, a n-propyl group ($CH_2CH_2CH_3$) and a t-butyl group ($C(CH_3)_3$);

provided the derivatives in which $R_6$ represents a benzyl group and $R_7$ represents a hydrogen atom at the same time, and the derivatives in which $R_6$ represents a p-hydroxybenzyl group and $R_7$ represents a hydrogen atom at the same time are excluded.

2. The derivative of claim 1, wherein $R_2$ is a hydroxyl group, $R_3$ is a methoxy group, $R_1$, $R_4$ and $R_5$ are hydrogen atoms, $R_6$ is a benzyl group, and $R_7$ and $R_8$ are methyl groups.

3. The derivative of claim 1, wherein $R_2$ is a methoxy group, $R_3$ is a hydroxyl group, $R_1$, $R_4$ and $R_5$ are hydrogen atoms, $R_6$ is a benzyl group, and $R_7$ and $R_8$ are methyl groups.

4. The derivative of claim 1, wherein $R_2$ is a hydroxyl group, $R_3$ is a methoxy group, $R_1$, $R_4$, $R_5$ and $R_7$ are hydrogen atoms, $R_6$ is a cyclohexylmethyl group, and $R_8$ is a methyl group.

5. The derivative of claim 1, wherein $R_2$ is a methoxy group, $R_3$ is a hydroxyl group, $R_1$, $R_4$, $R_5$ and $R_7$ are hydrogen atoms, $R_6$ is a cyclohexylmethyl group, and $R_8$ is a methyl group.

6. The derivative of claim 1, wherein $R_2$ is a hydroxyl group, $R_3$ is a methoxy group, $R_1$, $R_4$, $R_5$ and $R_7$ are hydrogen atoms, $R_6$ is a phenyl group, and $R_8$ is a methyl group.

7. The derivative of claim 1, wherein $R_2$ is a methoxy group, $R_3$ is a hydroxyl group, $R_1$, $R_4$, $R_5$ and $R_7$ are hydrogen atoms, $R_6$ is a phenyl group, and $R_8$ is a methyl group.

8. The derivative of claim 1, wherein $R_2$ is a hydroxyl group, $R_3$ is a methoxy group, $R_1$, $R_4$, $R_5$ and $R_7$ are hydrogen atoms, $R_6$ is a 2-phenylethyl group, and $R_8$ is a methyl group.

9. The derivative of claim 1, wherein $R_2$ is a methoxy group, $R_3$ is a hydroxyl group, $R_1$, $R_4$, $R_5$ and $R_7$ are hydrogen atoms, $R_6$ is a 2-phenylethyl group, and $R_8$ is a methyl group.

10. The derivative of claim 1, wherein $R_2$ is a hydroxyl group, $R_3$ is a methoxy group, $R_1$, $R_4$, $R_5$ and $R_6$ are hydrogen atoms, $R_7$ is a methyl group, and $R_8$ is a n-propyl group.

11. The derivative of claim 1, wherein $R_2$ is a methoxy group, $R_3$ is a hydroxyl group, $R_1$, $R_4$, $R_5$ and $R_6$ are hydrogen atoms, $R_7$ is a methyl group, and $R_8$ is a n-propyl group.

12. The derivative of claim 1, wherein $R_1$ is a hydroxyl group, $R_3$ is a methoxy group, $R_2$, $R_4$, and $R_5$ are hydrogen atoms, $R_6$ is a benzyl group, and $R_7$ and $R_8$ are methyl groups.

13. The derivative of claim 1, wherein $R_2$ and $R_8$ are methyl groups, $R_3$ is a hydroxyl group, $R_1$, $R_4$, $R_5$ and $R_7$ are hydrogen atoms, and $R_6$ is a cyclohexylmethyl group.

14. The derivative of claim 1, wherein $R_1$ is a hydroxyl group, $R_3$ and $R_8$ are methyl groups, $R_2$, $R_4$, $R_5$ and $R_7$ are hydrogen atoms, and $R_6$ is a cyclohexylmethyl group.

15. A composition comprising at least one derivative of claim 1 and a carrier or bulking agent.

16. A method of imparting sweetness into a substance comprising adding at least one derivative of claim 1 to said substance.

17. The method of claim 16, wherein said substance is selected from the group consisting of food, beverage, pharmaceutical product, and oral hygiene product.

18. A method of producing the derivative of claim 1, comprising reacting an aldehyde represented by the formulas (2) or (3) under reductive alkylation conditions

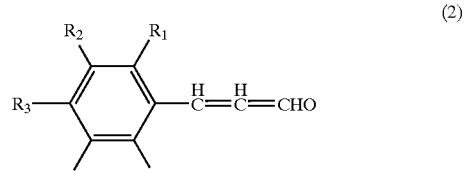

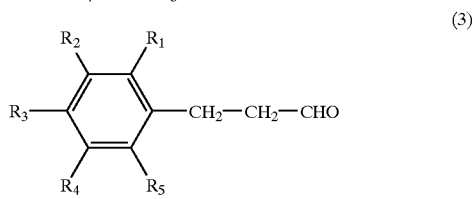

wherein $R_1$, $R_2$, $R_3$, $R_4$ and $R_5$ are the same as formula (1); with a aspartame derivative represented by the formula (4)

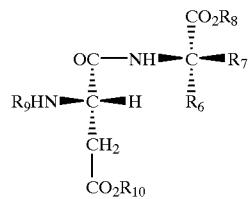

(4)

wherein $R_6$, $R_7$ and $R_8$ have the same meanings as those in the $R_6$, $R_7$ and $R_8$ in formula (1);

$R_9$ is a hydrogen atom or a substituent which is convertible to a hydrogen atom under reductive alkylation conditions; and $R_{10}$ is a hydrogen atom or a substituent which can be used for protecting a carboxyl group.

19. The method of claim 18, wherein $R_{10}$ is a benzyl group or a t-butyl group.

* * * * *